(12) United States Patent
Rosenblatt (10) Patent No.: US 7,338,502 B2
(45) Date of Patent: Mar. 4, 2008

(54) SYSTEMS AND METHODS FOR SOFT TISSUE RECONSTRUCTION

(75) Inventor: Peter L. Rosenblatt, West Newton, MA (US)

(73) Assignee: Rosenblatt Associates, LLC, Newton, MA (US)

( * ) Notice: Subject to any disclaimer, the term of this patent is extended or adjusted under 35 U.S.C. 154(b) by 445 days.

(21) Appl. No.: 10/740,132

(22) Filed: Dec. 18, 2003

(65) Prior Publication Data

US 2004/0186515 A1    Sep. 23, 2004

Related U.S. Application Data

(60) Provisional application No. 60/434,740, filed on Dec. 18, 2002.

(51) Int. Cl.
  *A61B 17/10*  (2006.01)
  *A61B 17/04*  (2006.01)
  *A61B 17/06*  (2006.01)
  *A61B 17/062* (2006.01)

(52) U.S. Cl. .................. 606/139; 606/144; 606/148; 606/222; 606/232

(58) Field of Classification Search ........... 606/139, 606/144, 148, 228, 232, 230, 222–225; 112/80.5, 112/169
See application file for complete search history.

(56) References Cited

U.S. PATENT DOCUMENTS

| 5,500,000 | A | * | 3/1996  | Feagin et al. ............... 606/232 |
| 5,628,756 | A | * | 5/1997  | Barker et al. ............... 606/139 |
| 5,643,295 | A | * | 7/1997  | Yoon ............................. 606/151 |
| 5,713,910 | A |   | 2/1998  | Gordon et al. |
| 6,048,351 | A |   | 4/2000  | Gordon et al. |
| 6,086,608 | A | * | 7/2000  | Ek et al. ..................... 606/232 |
| 6,096,051 | A |   | 8/2000  | Kortenbach et al. |
| 6,332,888 | B1 |  | 12/2001 | Levy et al. |
| 6,454,778 | B2 |  | 9/2002  | Kortenbach |
| 6,475,135 | B1 |  | 11/2002 | Levy et al. |
| 6,551,329 | B1 |  | 4/2003  | Kortenbach et al. |
| 6,923,819 | B2 | * | 8/2005 | Meade et al. ............... 606/144 |
| 6,981,983 | B1 | * | 1/2006 | Rosenblatt et al. ......... 606/216 |
| 7,033,379 | B2 | * | 4/2006 | Peterson ..................... 606/232 |
| 7,048,749 | B2 |  | 5/2006  | Kortenbach et al. |
| 7,048,755 | B2 | * | 5/2006 | Bonutti et al. .............. 606/232 |

* cited by examiner

*Primary Examiner*—Anhtuan T. Nguyen
*Assistant Examiner*—Amy T. Lang
(74) *Attorney, Agent, or Firm*—Scott E. Kamholz; Foley Hoag LLP (57) ABSTRACT

Suture-based fasteners and fastening methods for soft tissue reconstruction are described that can include a needle tip swaged onto two sutures and loaded onto the end of a curved needle shaft. The needle shaft and tip can be driven through the tissues to be sutured and back out to where the needle tip can make a permanent connection with a locking bead. The needle shaft can be retracted, leaving two sutures extending from the side of the bead. One suture can be of nonabsorbable material and can be brought through the end of the locking bead opposite the tip and pulled to tighten the suture loop. The other suture can be of an absorbable material and can be used to rotate the locking bead under one of the layers of tissue being sutured after the suture loop is tightened. Following rotation, the second suture can be trimmed.

17 Claims, 7 Drawing Sheets

SYSTEMS AND METHODS FOR SOFT TISSUE RECONSTRUCTION

RELATED APPLICATIONS

This application claims priority to, and incorporates by reference, the entire disclosure of U.S. Provisional Patent Application No. 60/434,740, filed on Dec. 18, 2002.

TECHNICAL FIELD

The invention relates generally to the use of soft tissue fixation devices and application instruments and accessories used in reconstructive soft tissue surgery.

BACKGROUND OF THE INVENTION

Surgical procedures often involve the apposition of tissues with the use of sutures or other devices, such as metallic clips or staples. Reconstructive surgical procedures depend on the permanent approximation of tissues, usually with the use of nonabsorbable suture material. In pelvic reconstructive surgery, for example, several approaches are commonly used to treat various types of pelvic support defects, including cystocele, rectocele, enterocele, uterine prolapse or vaginal vault prolapse after hysterectomy. Abdominal or laparoscopic surgery may be used to elevate the urethra or bladder, the uterus or vaginal vault. Sutures may be placed under the vaginal epithelium in order to suspend the vagina to supporting structures, such as the pelvic side wall, the arcus tendineous fascia pelvis, the sacrospinous ligament, Uterosacral ligament, Cooper's ligament, the pubic symphysis or the anterior longitudinal ligament of the sacral promontory. Vaginal reconstructive surgery may utilize some of the same supporting structures, although the vaginal wall must be opened either anteriorly, posteriorly or apically, in order to place the suspending sutures under the vaginal epithelium. Although vaginal surgery is associated with decreased morbidity, length of stay and recovery compared with abdominal surgery, there is evidence that it may lead to greater denervation and increased rates of recurrent prolapse and need for reoperation. There exists a need in reconstructive and other types of surgery to create a system whereby tissues may be approximated in a minimally-invasive and automated fashion.

SUMMARY OF THE INVENTION

Fasteners may be designed to recreate the basic concept of sutures, which may appeal to surgeons who feel more comfortable with standard suturing techniques for surgery, including pelvic reconstructive surgery. For example, transvaginal surgery including paravaginal cystocele repair may be performed without the need for a mucosal incision. It is desirable to avoid having a knot within the vaginal lumen. After the area of the arcus tendineous fascia pelvis is palpated vaginally between the posterior-lateral aspect of the pubic bone and the ischial spine, a series of fasteners may be placed along the arcus tendineous fascia pelvis, reapproximating the vaginal wall to the pelvic sidewall and reestablishing the position of the lateral vaginal sulci. Having a tight suture loop without a knot in the vagina may promote reepithelialization, whereas the presence of a suture knot may prevent the vaginal mucosa from healing over the suture. In the present invention, suture-based fasteners are described that, when deployed, result in a knot-free, tight suture loop. In transvaginal reconstructive surgery, for example, this configuration may promote reepithelialization of suture material in the vaginal lumen.

In one embodiment, a method of connecting a first layer of tissue and a second layer of tissue can include providing a loop in a suture to form a loop end, driving the loop end and/or a combination of the loop end and an end of the suture on a path through the first layer, into the second layer, and back through the first layer, engaging the loop end with an engaging mechanism located proximate the end of the suture to form a closed ring, tightening the closed ring by drawing the loop end back along the path, and rotating the ring to place the engaging mechanism within the second layer.

In one embodiment, a system for connecting a first layer of tissue and a second layer of tissue can include a suture, a loop in the suture to form a loop end of the suture, means for driving at least one of the loop end and a combination of the loop end and an end of the suture on a path through the first layer, into the second layer, and back through the first layer, engaging means proximate the end of the suture engaging the loop end to form a closed ring, means for tightening the closed ring by drawing the loop end back along the path, and means for rotating the ring to place the engaging means within the second layer.

DETAILED DESCRIPTION OF THE INVENTION

To provide an overall understanding, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the disclosed systems or methods.

The invention will now be described with reference to certain illustrated embodiments and certain exemplary practices. Specifically, the invention will be described hereinafter in connection with soft tissue reconstructive medical procedures, described in more detail below, and with urogynecological reconstruction. As used herein, the invention can be used to connect two layers of tissue, which can be referred to herein as a pelvic sidewall, vaginal lumen, vaginal mucosa, or other similar tissues. However, it should be understood that the following description is only meant to be illustrative of the invention and is not meant to limit the scope of the invention, which is applicable to other forms of soft tissue reconstruction, as will be evident to practitioners in the art.

In certain embodiments, the common theme is to create a knot or other type of attachment of two ends of a suture and then to rotate the "knot" under the mucosa, so that only a tight suture loop remains in the vaginal lumen.

Figure 1A:
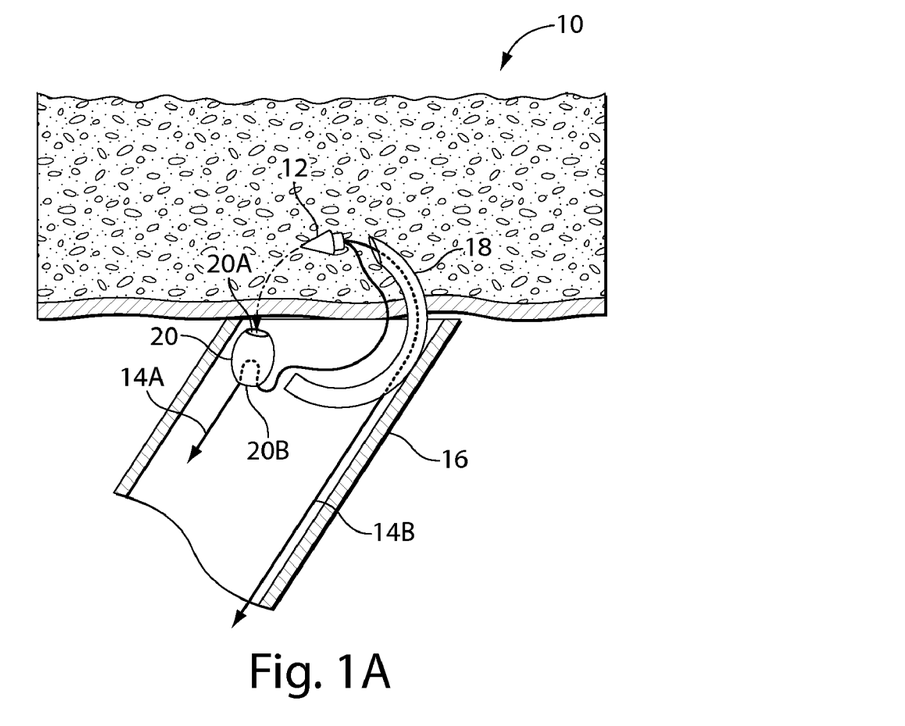
FIGS. 1A-1C illustrate tissue undergoing reconstruction using one embodiment of a fastener having an engaging mechanism for tightening the suture.
Figure 1B:
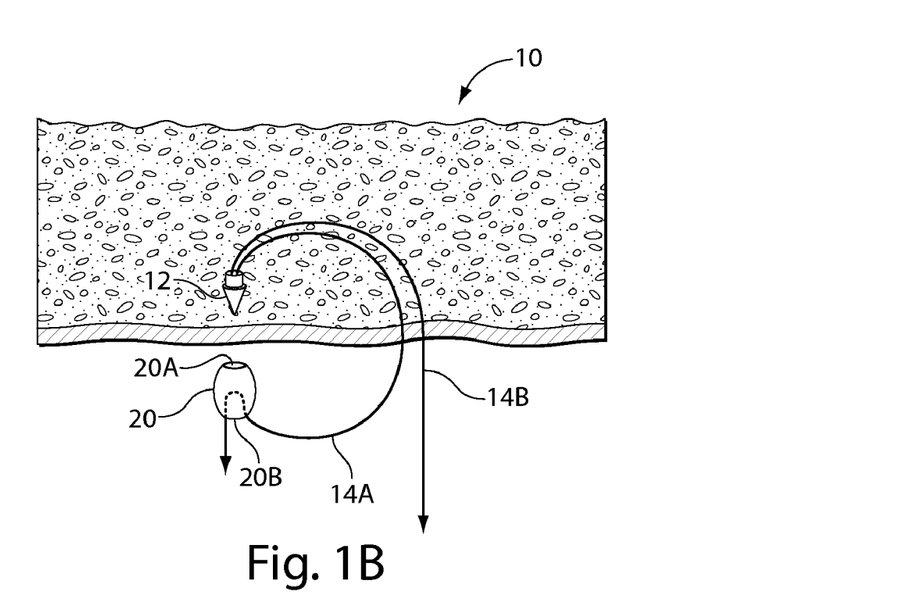
Figure 1C:
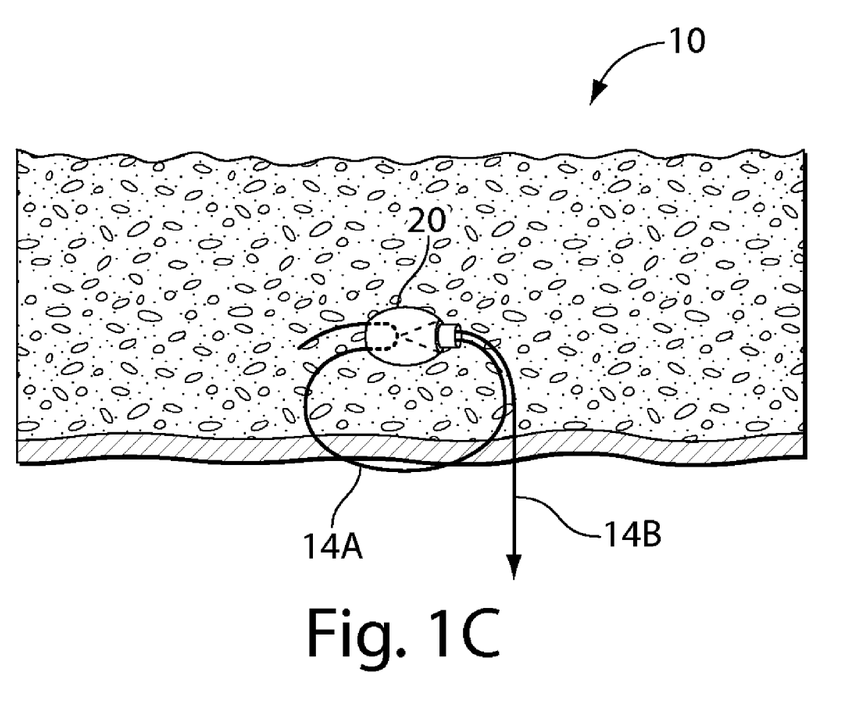

In one embodiment 10 (FIGS. 1A-1C), a needle tip 12 is swaged on to two sutures, 14A, 14B which are loaded in a hand-held instrument 16. The needle tip is loaded on to the end of a curved needle shaft 18, in a manner similar to a Capio needle driver. Pushing a piston-type button (not shown) drives the needle shaft with pre-loaded needle tip through the tissue and back into the instrument, where the needle tip makes a permanent connection with a locking bead 20, which has a female end 20A, in which the needle tip will connect (FIG. 1B). The needle shaft is then retracted back into the instrument. There are two sutures that come out from the side of the bead where the male and female ends are connected, sutures 14A and 14B. Suture 14A is engaged with the other end of the locking bead 20B, which is made of either a plastic or metal material. This suture segment may be of nonabsorbable material. The end of suture 14A is pulled after the connection is made between the needle tip and the locking bead, in order to tighten the suture loop, which recreates the tightness of a standard suture loop. The other suture 14B is used to rotate the locking bead under the vaginal mucosa after the connection between the needle tip and locking bead is made, and after the suture loop is tightened (FIG. 1C). Following this rotation of the locking bead, the second suture must be trimmed under the vaginal mucosa. This second suture may be made of absorbable material.

Figure 2A:
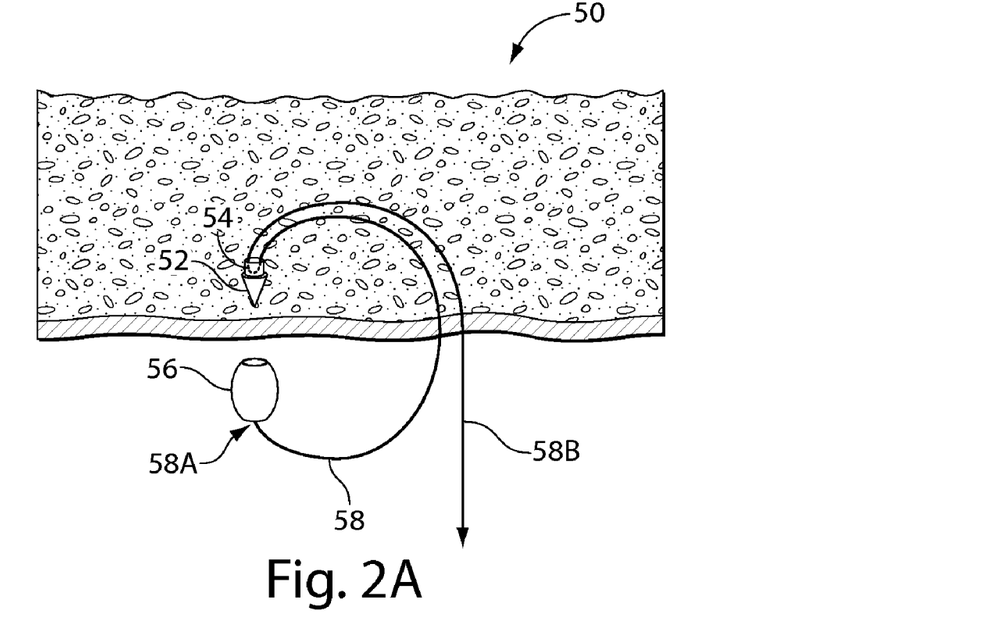
FIGS. 2A-2B illustrate tissue undergoing reconstruction using one embodiment of a fastener having an engaging mechanism and a separate suture-tightening mechanism.
Figure 2B:
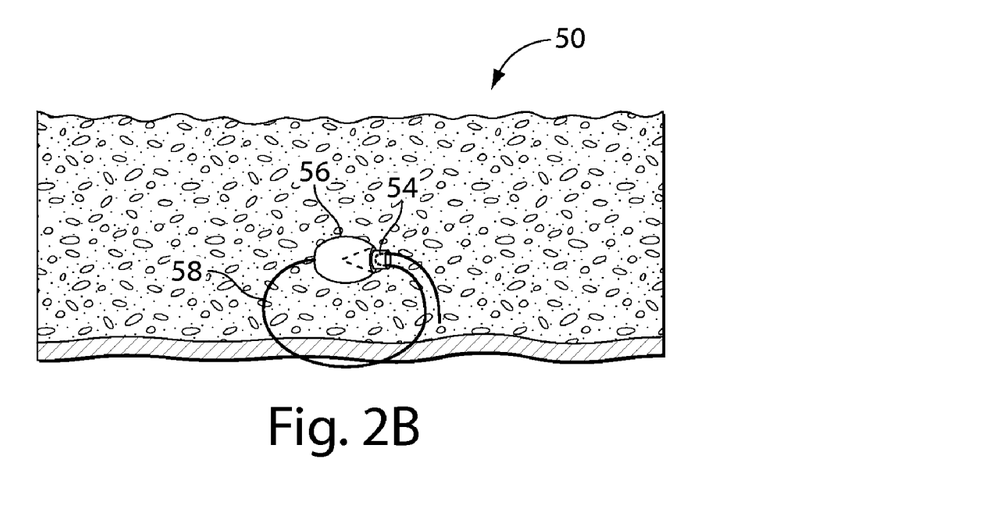

In another embodiment 50 (FIGS. 2A-2B), the needle tip 52 (which is pushed through the tissue with a retractable needle shaft, as in the Capio needle driver) has an attached suture tightening mechanism 54, similar to the mechanism used to tighten a backpack strap. When the needle is driven through the tissue, the tip connects to the female locking bead 56, which is attached to one end 58A of the suture 58 (FIG. 2A). The locking bead is located and held in position in the instrument. Pulling on the other end 58B of the suture 58 initially tightens the suture loop, and then rotates the locking bead under the vaginal mucosa (FIG. 2B). The instrument may have a mechanism that holds the locking bead in place during the tightening process, and then releases the locking bead so that it may rotate under the mucosa. The holding mechanism may release the locking bead when a predetermined tension is attained, or may be manually released by the surgeon after the suture is tightened. The suture is then trimmed under the vaginal mucosa. This is accomplished with a cutting blade located within the instrument and cuts the suture even with the most distal portion of the instrument.

Figure 3A:
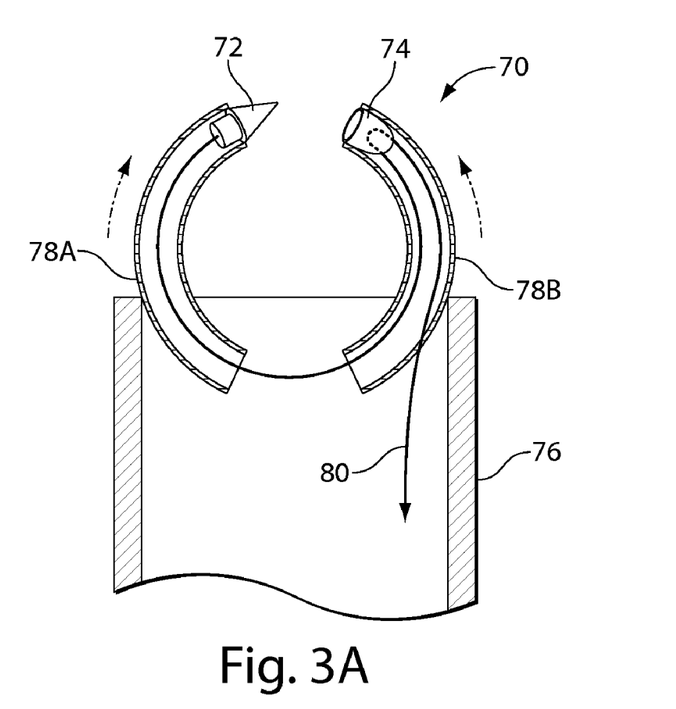
FIGS. 3A-3B illustrate tissue undergoing reconstruction using one embodiment of a fastener having an engaging mechanism and a separate suture-tightening mechanism being both driven into the tissue.
Figure 3B:
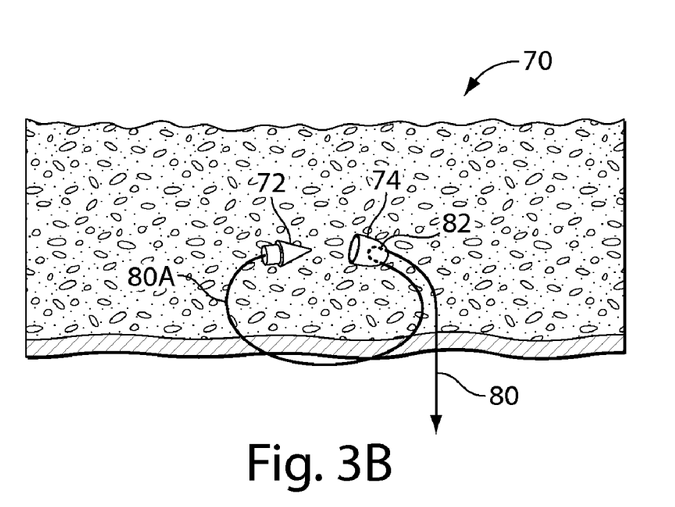

In another embodiment 70 (FIGS. 3A-3B), the connection between the male (needle tip 72) and female (locking bead 74) ends is made within the pelvic sidewall. This is done by pushing a button (not shown) on the end of the instrument 76, which deploys the two hollow needle shafts 78A, 78B. The needle shafts pierce the vaginal wall and meet under the pelvic sidewall, which automatically locks the male and female ends together (FIG. 3A). By releasing the button, the needle shafts are retracted, leaving the connection within the tissue (FIG. 3B). After the connection is made, the suture 80 that comes out through the female portion of the bead, or cleat 82, is pulled, which tightens the suture loop 80A. The suture is then trimmed under the vaginal mucosa. This is accomplished with a cutting blade (not shown) located within the instrument and cuts the suture even with the most distal portion of the instrument.

Figure 4A:
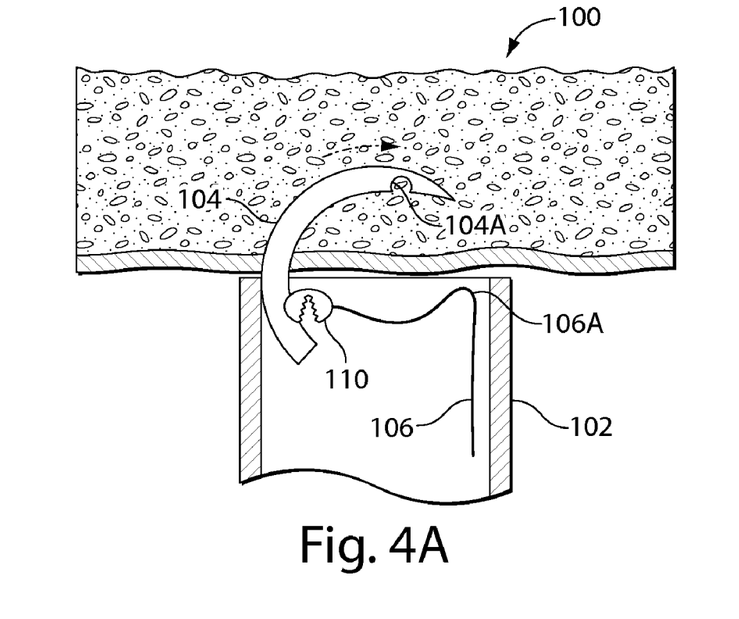
FIGS. 4A-4E illustrate tissue undergoing reconstruction using one embodiment of a fastener having mechanism for pulling a suture through the tissue.
Figure 4B:
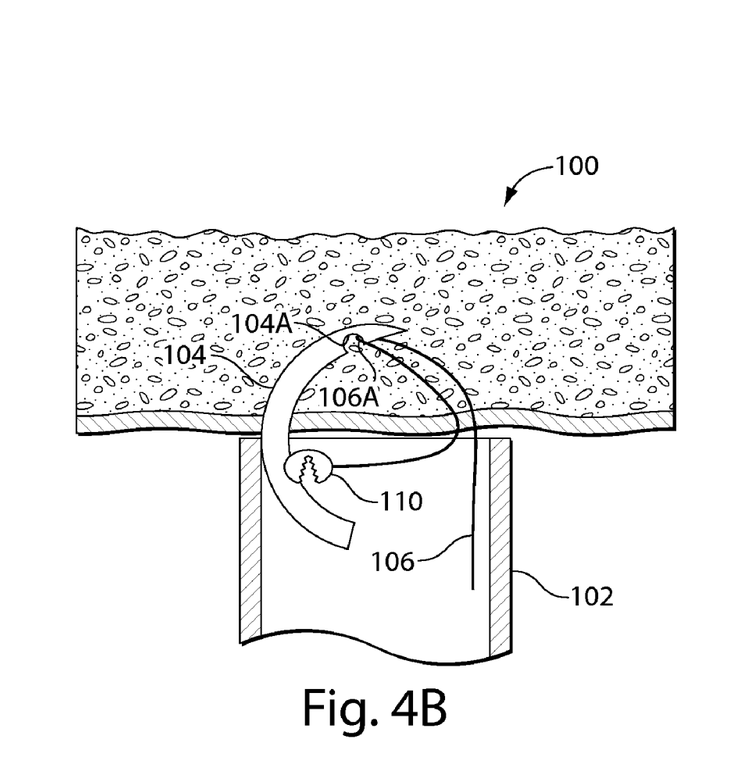
Figure 4C:
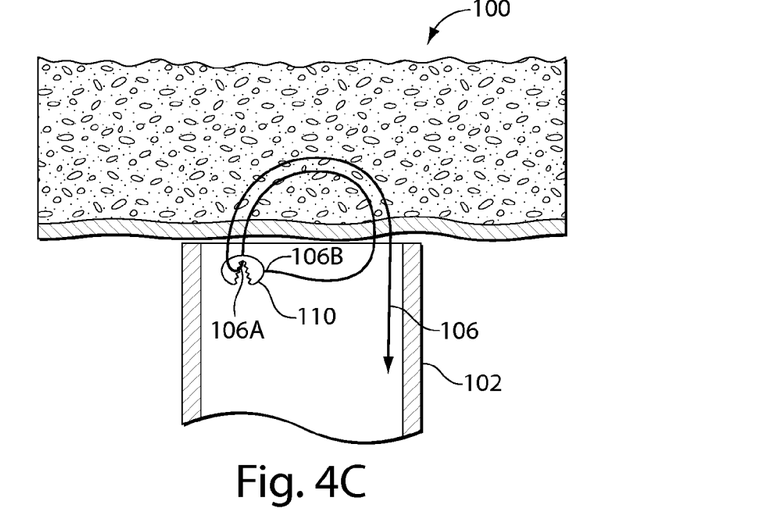
Figure 4D:
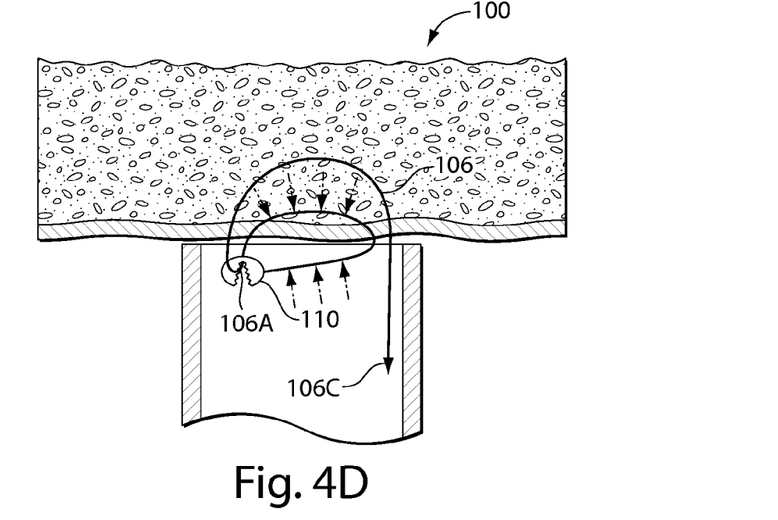
Figure 4E:
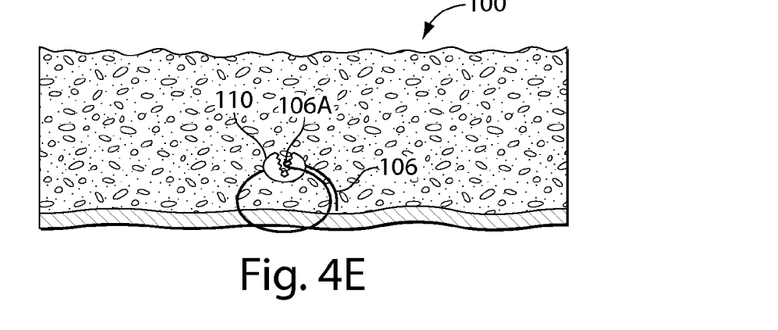

In another embodiment 100 (FIGS. 4A-4E), pushing a piston-like button (not shown) on the proximal end of the instrument 102 pushes a notched curved needle 104 located at the distal end of the instrument through the pelvic sidewall (FIG. 4A) and upon exiting the tissue, a loop 106A of suture 106 located in the distal instrument is captured by the notch 104A of the needle and pulled back through the tissue (FIG. 4B) and back into the instrument. One end of this suture loop is then brought through a locking cleat 110, which is attached to one end 106B of the suture 106 (FIG. 4C). This locking cleat may be metallic or plastic and is held in place in the distal end of the instrument. Although it may take one of a number of configurations, the basic concept of the cleat is that it captures a strand of suture, and pulling on the other end 106C of the suture loop (which resides within the instrument) makes the knot encompassing the tissue tighter and tighter (FIG. 4D). Once a predetermined suture tension is attained, or when the surgeon determines that the tension is appropriate by other means, the cleat is released by the instruments, which then permits rotation of the locking cleat under the vaginal mucosa or lumen (FIG. 4E). The suture is then trimmed under the vaginal mucosa. This is accomplished with a cutting blade located within the instrument and cuts the suture even with the most distal portion of the instrument.

Figure 5A:
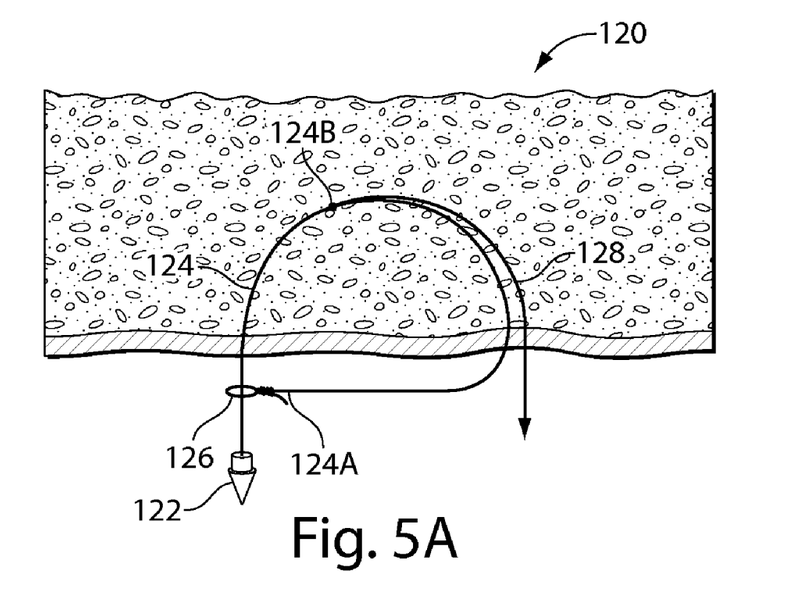
FIGS. 5A-5B illustrate tissue undergoing reconstruction using one embodiment of a fastener having an engaging mechanism formed from the suture.
Figure 5B:
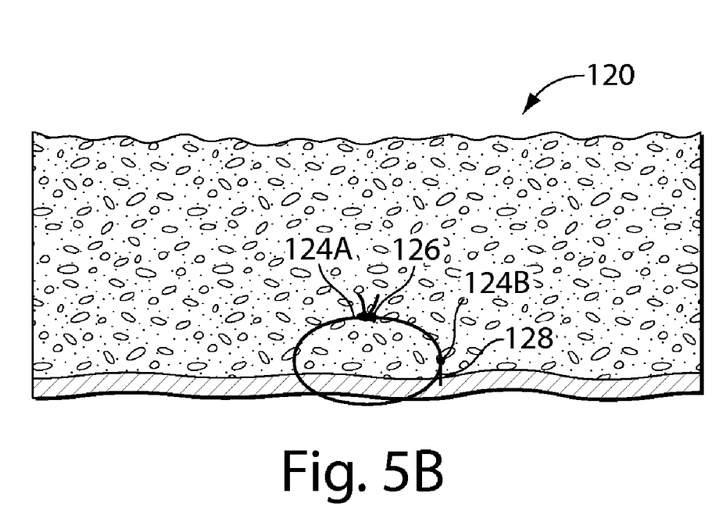

In another embodiment 120 (FIGS. 5A-5B), a hollow needle shaft (not shown) (similar to a Capio needle driver) is used to carry a pre-loaded needle tip 122 with a single swaged suture 124 through a preformed open "hitch" knot 126 connected to an end 124A of suture 124 opposite the needle tip on the other side of the instrument (not shown). The needle tip then makes a connection with a female element (not shown) within the instrument. A mechanism (not shown) that pulls back on the female element (after connection is made with the needle tip) tightens the hitch knot. The suture on the needle tip is cut near the preformed knot and a second suture 128, attached at a point 124B to the primary suture 124, is used to rotate the knot under the vaginal mucosa or lumen. The second suture is then trimmed under the vaginal mucosa. This is accomplished with a cutting blade located within the instrument and cuts the suture even with the most distal portion of the instrument.

Unless otherwise stated, use of the word "substantially" can be construed to include a precise relationship, condition, arrangement, orientation, and/or other characteristic, and deviations thereof as understood by one of ordinary skill in the art, to the extent that such deviations do not materially affect the disclosed methods and systems. Throughout the entirety of the present disclosure, use of the articles "a" or "an" to modify a noun can be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, can be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. Many additional changes in the details, materials, and arrangement of parts, herein described and illustrated, can be made by those skilled in the art. Accordingly, it will be understood that the following are not to be limited to the embodiments disclosed herein, can include practices otherwise than specifically described, and are to be interpreted as broadly as allowed under the law.

What is claimed is:

1. A suturing system comprising:
   a shaft having a distal end;
   a curved hollow tube so disposed in the distal end of the shaft as to be rotatable in a curved path that runs out of a plane that is defined by the distal end and oblique to a main axis of the shaft;
   a detachable sharpened tip disposed on a distal end of the curved hollow tube;
   at least one suture attached to the detachable sharpened tip; and
   a receptacle that is:
      threaded on the suture;
      positioned in the curved path; and
      so sized and shaped as to engage the detachable sharpened tip so that the sharpened tip is detached from the curved tube when the receptacle engages the tip.

2. A suturing system comprising:
   a shaft having a distal end;
   a curved hollow tube so disposed in the distal end of the shaft as to be rotatable in a curved path that runs out of a plane that is defined by the distal end and oblique to a main axis of the shaft;
   a detachable sharpened tip disposed on a distal end of the curved hollow tube, wherein the sharpened tip is detached from the curved tube during normal use;
   a first suture having a first end and a second end, wherein:
      the first suture is attached at its first end to the detachable sharpened tip;
      the second end of the first suture is formed as a hitch knot defining a loop large enough to allow the detachable sharpened tip to pass therethrough;
      the loop is positioned in the curved path; and
      the hitch knot is so tightenable as to grip the first suture; and
   a second suture attached to the first suture at a position between the first and second ends of the first suture.

3. The system of claim 1, wherein the receptacle defines an orifice so sized and shaped as to receive and engage the detachable sharpened tip and to prevent disengagement of the tip from the receptacle.

4. The system of claim 1, wherein the receptacle comprises a tightening mechanism sized and positioned to receive the suture.

5. The system of claim 4, wherein the tightening mechanism comprises a cleat sized and positioned to permit advancement of the suture through the cleat in a direction that permits tightening of a suture loop, formed when the detachable sharpened tip engages the receptacle, and to prevent advancement of the suture through the cleat in an opposite direction.

6. A method of approximating first and second structures, comprising:
   positioning the shaft distal end of the system of claim 1 next to the first structure;
   advancing the detachable sharpened tip and the curved hollow tube through the first structure and the second structure, thereby drawing the suture through the structures;
   engaging the sharpened tip with the receptacle; and
   disengaging the sharpened tip from the curved tube; thereby forming a loop of suture approximating the first and second structures.

7. The method of claim 6, wherein engaging comprises irreversibly engaging the sharpened tip with the receptacle.

8. The method of claim 6, further comprising so rotating the loop of suture as to position the engaged tip and receptacle in at least one of the first and second structures.

9. The method of claim 6, further comprising tightening the loop of suture.

10. The method of claim 9, wherein the receptacle comprises a cleat through which the suture is irreversibly drawn to tighten the loop of suture.

11. The system of claim 2, wherein the shaft further comprises a receptacle that is positioned in the curved path and so sized and shaped as to engage the detachable sharpened tip so that the sharpened tip is detached from the curved tube when the receptacle engages the tip.

12. The method of claim 6, wherein the first layer of tissue defines a lumen on a first side, and the second layer of tissue is located next to another side of the first layer.

13. A method of approximating first and second structures, comprising:
   positioning the shaft distal end of the system of claim 2 next to the first structure;
   advancing the detachable sharpened tip and the curved hollow tube through the first structure and the second structure, thereby drawing the first suture through the structures;
   passing the sharpened tip through the loop of the hitch knot so that the first suture passes through the hitch knot loop;
   disengaging the sharpened tip from the curved tube; and
   tightening the hitch knot to grip the first suture, thereby forming a loop of suture approximating the first and second structures.

14. The method of claim 13, further comprising so rotating the loop of suture as to position the tightened hitch knot in at least one of the first and second structures.

15. The method of claim 14, wherein the loop of suture is rotated by pulling the second suture.

16. The method of claim 13, further comprising tightening the loop of suture.

17. The method of claim 13, further comprising removing the sharpened tip from the first suture.

* * * * *